United States Patent [19]

Kinkead

[11] Patent Number: 5,607,647
[45] Date of Patent: Mar. 4, 1997

[54] AIR FILTERING WITHIN CLEAN ENVIRONMENTS

[75] Inventor: Devon A. Kinkead, Cumberland, R.I.

[73] Assignee: Extraction Systems, Inc., Woonsocket, R.I.

[21] Appl. No.: 317,315

[22] Filed: Oct. 4, 1994

Related U.S. Application Data

[63] Continuation-in-part of Ser. No. 161,931, Dec. 2, 1993.

[51] Int. Cl.$^6$ .............. A61L 9/00; B01D 53/34; B01D 46/00; B01L 1/04
[52] U.S. Cl. .............. 422/122; 422/171; 422/177; 454/187; 95/285; 95/287; 96/135; 55/485; 55/524
[58] Field of Search .............. 422/122, 169, 422/170, 171, 177; 454/187, 53; 95/285, 287; 96/135; 55/284, 315, 318, 350.1, 482, 485, 524; 250/492.2

[56] References Cited

U.S. PATENT DOCUMENTS

| | | | |
|---|---|---|---|
| 1,585,113 | 5/1926 | Robert | 96/136 |
| 3,015,367 | 1/1962 | Smith et al. | 96/135 |
| 3,170,808 | 2/1965 | Almy et al. | 427/559 |
| 3,196,871 | 7/1965 | Hormats et al. | 128/205.28 |
| 3,220,915 | 11/1965 | Shannon | 428/194 |
| 3,226,251 | 12/1965 | Norton et al. | 427/244 |
| 3,294,572 | 12/1966 | Piccione et al. | 427/229 |
| 3,375,933 | 4/1968 | Rodman | 210/502.1 |
| 3,381,454 | 5/1968 | Sponsel | 502/159 |
| 3,525,378 | 8/1970 | Root | 160/1 |
| 3,690,852 | 9/1972 | Smith et al. | 427/201 |

(List continued on next page.)

FOREIGN PATENT DOCUMENTS

| | | |
|---|---|---|
| 88225 | 7/1895 | Germany. |
| 54-34475 | 3/1979 | Japan. |
| 55-48851 | 9/1980 | Japan. |
| 61-262537 | 11/1986 | Japan. |
| 62-129142 | 6/1987 | Japan .................. 422/122 |

(List continued on next page.)

OTHER PUBLICATIONS

Saiki et al., Development of Ammonia Adsorption Filter and Its Application to LSI Manufacturing Environment, Jpn. J. Appl. Phys., vol. 33, pp. 2504–2508, May 1994.

Martin Ferm, Method for Determination of Atmospheric Ammonia, Atmospheric Environment, vol. 13, pp. 1385–1393,, 1979.

Muller et al., "Measurement of Airborne Concentrations and Surface Arrival Rates of Organic Contaminants in Clean Rooms", AT&T Bells Labs, Murray Hill, NJ, 1993 IES-AJM.

(List continued on next page.)

*Primary Examiner*—Robert J. Warden
*Assistant Examiner*—E. Leigh Dawson
*Attorney, Agent, or Firm*—Fish & Richardson P.C.

[57] ABSTRACT

An air filtering system for filtering air streams for use in a clean environment to effectively remove a process-limiting molecular contaminant therefrom comprising sequentially arranged upstream and downstream air filtering beds. The upstream air filtering bed is positioned to receive an air stream for use in the clean environment and comprises an upstream reagent selected to effectively remove the process-limiting molecular contaminant from the air stream as the air stream passes through the upstream air filtering bed, the upstream reagent releasing a characteristic volatile component into the air streams. The downstream air filtering bed is positioned to receive the air stream that has passed through the upstream air filtering bed and comprises a downstream reagent selected to remove the characteristic volatile component released by the upstream reagent into the air stream. Clean environments (e.g., a deep UV processing station) incorporating the above-mentioned air filtering system are also disclosed.

35 Claims, 6 Drawing Sheets

U.S. PATENT DOCUMENTS

| | | | |
|---|---|---|---|
| 3,697,347 | 10/1972 | Lebruann | 156/181 |
| 3,779,244 | 12/1973 | Weeks, Jr. et al. | 128/206.19 |
| 3,800,516 | 4/1974 | Paluch | 96/150 |
| 3,862,420 | 1/1975 | Banks | 55/485 |
| 3,870,495 | 3/1975 | Dixson et al. | 55/489 |
| 3,912,567 | 10/1975 | Schwartz | 156/167 |
| 3,925,021 | 12/1975 | Yoshino et al. | 96/118 |
| 3,998,988 | 12/1976 | Shimomai et al. | 428/400 |
| 4,007,301 | 2/1977 | De Martino | 427/244 |
| 4,011,067 | 3/1977 | Carey, Jr. | 55/354 |
| 4,075,282 | 2/1978 | Storp et al. | 423/230 |
| 4,081,501 | 3/1978 | Muther | 264/518 |
| 4,132,650 | 1/1979 | Kirsch et al. | 210/491 |
| 4,160,059 | 7/1979 | Samejima | 428/288 |
| 4,171,410 | 10/1979 | Frob | 521/52 |
| 4,188,960 | 2/1980 | Morie et al. | 131/345 |
| 4,201,838 | 5/1980 | Goldberg | 429/145 |
| 4,204,011 | 5/1980 | Tanabe et al. | 427/57 |
| 4,215,682 | 8/1980 | Kubik et al. | 128/205.29 |
| 4,225,642 | 9/1980 | Hirawaka | 428/91 |
| 4,285,748 | 8/1981 | Booker et al. | 156/167 |
| 4,315,965 | 2/1982 | Mason et al. | 428/198 |
| 4,344,775 | 8/1982 | Klein | 95/137 |
| 4,370,301 | 1/1983 | Doi et al. | 422/122 |
| 4,376,675 | 3/1983 | Perrotta | 162/145 |
| 4,379,802 | 4/1983 | Weaver et al. | 428/220 |
| 4,530,272 | 7/1985 | Stokes | 454/187 |
| 4,578,256 | 3/1986 | Nishino et al. | 423/210 |
| 4,595,575 | 6/1986 | Oeste et al. | 423/210 |
| 4,643,182 | 2/1987 | Klein | 128/201.25 |
| 4,664,683 | 5/1987 | Degen et al. | 502/402 |
| 4,680,040 | 7/1987 | Gooray et al. | 96/152 |
| 4,693,173 | 9/1987 | Saiki et al. | 454/187 |
| 4,696,837 | 9/1987 | Lindner | 427/255.3 |
| 4,699,681 | 10/1987 | Kasmark, Jr. et al. | 55/316 |
| 4,704,972 | 11/1987 | Marchand | 110/345 |
| 4,737,173 | 4/1988 | Kudirka et al. | 55/276 |
| 4,792,491 | 12/1988 | Atkinson et al. | 428/408 |
| 4,793,837 | 2/1988 | Pontius | 502/62 |
| 4,873,914 | 10/1989 | Hirayama | 454/187 |
| 4,983,192 | 1/1991 | von Blücher et al. | 55/387 |
| 4,985,280 | 1/1991 | Scholz et al. | 427/244 |
| 5,015,451 | 5/1991 | Holter et al. | 55/318 |
| 5,030,423 | 7/1991 | Obee et al. | 422/122 |
| 5,037,624 | 8/1991 | Tom et al. | 423/210 |
| 5,042,997 | 8/1991 | Rhodes | 96/18 |
| 5,053,064 | 10/1991 | Hama et al. | 96/111 |
| 5,064,626 | 11/1991 | Johnson et al. | 423/245.1 |
| 5,096,477 | 3/1992 | Shinoda et al. | 454/187 |
| 5,143,752 | 9/1992 | Nakajima et al. | 427/244 |
| 5,165,595 | 11/1992 | Horio et al. | 236/49.3 |
| 5,166,530 | 11/1992 | McCleary | 250/492.2 |
| 5,169,418 | 12/1992 | Honda et al. | 55/268 |
| 5,181,819 | 1/1993 | Sakata et al. | 454/187 |
| 5,213,767 | 5/1993 | Smith et al. | 422/177 |
| 5,260,580 | 11/1993 | Itoh et al. | 250/492.2 |
| 5,271,780 | 12/1993 | Baigas, Jr. | 156/62.6 |
| 5,271,997 | 12/1993 | Baigas, Jr. | 428/233 |
| 5,288,306 | 2/1994 | Aibe et al. | 96/135 |
| 5,434,644 | 7/1995 | Kitano et al. | 355/30 |

FOREIGN PATENT DOCUMENTS

| | | | |
|---|---|---|---|
| 2-126912 | 5/1990 | Japan. | |
| 433186 | 9/1935 | United Kingdom. | |
| 2013102 | 6/1976 | United Kingdom. | |
| 2005016 | 9/1978 | United Kingdom. | |
| 2034598 | 6/1980 | United Kingdom | 422/122 |
| 2077141 | 4/1981 | United Kingdom. | |
| WO90/05549 | 5/1990 | WIPO. | |

OTHER PUBLICATIONS

Kelly et al., "Testing of chemically treated adsorbent air purifiers", ASHRAE Journal Jul. 1993.

Devon Kinkead, "Controlling a Killer: How to Win the War Over Gaseous Contaminants", CleanRooms Magazine Jun. 1993.

Kinkead et al., "Targeting Gaseous Contaminants in Wafer Fabs: Fugitive Amines", Microcontamination Jun. 1993.

Extraction Systems, Inc. Catalogue (1992).

Mori et al., "Correlating Organophosphorus Contamination on Wafer Surfaces with Hepa–Filter Installation", Microcontamination Nov. 1992.

EACI/Envirco Bulletin, "Check Our Room–Side Manner", 1992.

MacDonald et al., "Airborne Chemical Contamination of a Chemically Amplified Resist", SPIE vol. 1466 (1991).

Kajuna et al., "Gas Adsorption on Wafers", Microelectronics Manufacturing Technology Dec. 1991.

Stevie et al., "Boron Contamination on surfaces in silicon microelectronics processing", J. Vac. Sci. 1991.

Devon A. Kinkead, Pleated DPCC–based adsorbers: New technology for air purification, ASHRAE Journal Nov. 1990.

Slade et al., "Utilization of Established Air Pollution Monitoring Networks in Ontario Following Nuclear Incidents", Radiation and Industrial Safety Branch Chalk River Nuclear Laboratories Apr. 1988.

Devon A. Kinkead, "The Incorporation and Use of Reagent Impregnated Activated Carbons in Nonwoven Webs, American Filtration Society", Mar. 1988.

Muller et al., Detection and Sources of Volatile Clean Room Contaminants, AT&T Bell Laboratories; AT&T Microelectronics.

David Jenson, "State of the Contamination Control Industry", Northern New England Chapter Institute of Environmental Sciences (Before Oct. 1993).

Extraction Systems Inc., Bulletin No. 020691–2, "What do HVAC odor/corrosion control systems and easy maintenance have in common?" (Before Oct. 1993).

Kinkead et al., "Semiconductor Process Stabilization", Extraction Systems, Inc. (Before Oct. 1993).

Extraction Systems Inc., Advertisement (Before Oct. 1993).

Foss Bulletin, "Engineered Nonwoven Fabrics" (Before Oct. 1993).

Lewcott Corp. Bulletin, "Activfilter Activated Carbon Impregnated Media New Technology for Removal of Odors, Contaminants, Pollutants and Irritants" (Before Oct. 1993).

Nanosorb™ 101–20 Activated Carbon Pad Bulletin (Before Oct. 1993).

AIR FILTERING WITHIN CLEAN ENVIRONMENTS

CROSS REFERENCE TO RELATED APPLICATIONS

This application is a continuation-in-part of U.S. patent application Ser. No. 08/161,931, filed Dec. 2, 1993.

BACKGROUND

This application relates to air filtering inside clean environments.

Air filtering is critical within environments that must remain clean, such as semiconductor device manufacturing environments. Tremendous efforts are made to eliminate process-limiting contaminants from the semiconductor device manufacturing site, commonly referred to as a clean room. Clean room contaminants may be generally classified as either particulate or molecular. Common particulate contaminants include dust, lint and other debris. Examples of process-limiting molecular contaminants include: acids, such as hydrochloric acid, nitric acid, phosphoric acid, hydrobromic acid; bases, such as ammonia, ammonium hydroxide, tetramethylammonium hydroxide, trimethylamine, triethylamine, hexamethyldisilazane, NMP, cyclohexylamine, diethylaminoethanol, methylamine, dimethylamine, ethanolamine, morpholine, condensables, such as silicones and hydrocarbons with a boiling point greater than or equal to 150° C.; and dopants, such as boron (usually as boric acid), phosphorus (usually as organophosphate), and arsenic (usually in the form of arsenates).

Most of the efforts in clean room design have focused on removing particulate contaminants from the constituent airstreams, because particulate contaminants were viewed as having the most impact on device yields and device performance. Recently, it has been realized that molecular contamination can impose severe limitations on further reduction of device geometry and improvement of device performance.

Molecular air contaminants are actually collections of molecules, unlike particulate contaminants, and are most easily distinguished from particulates by size. Very small particulate matter may be about 1200 angstroms in diameter, while molecular contaminants are typically only a fraction of an angstrom in diameter (about 30,000–40,000 times smaller than typical particulate contaminants). This size differential translates into entirely different removal mechanisms for molecular and particulate contaminants. Two common molecular contaminant removal techniques are adsorption/condensation and chemisorption.

Unlike particulate matter, molecular air pollutants possess specific chemical and physical properties unique to the chemical specie they represent. The boiling point, vapor pressure, and reactivity characteristics of the molecular pollutants are especially important in the design of molecular air purification equipment. Generally, molecular contaminants with a boiling point of 100° C. or greater may be effectively removed using activated carbon alone (by adsorption/condensation mechanisms), while removal of contaminants with lower boiling points (e.g., organophosphate, ammonia and other reactive amines) requires some sort of chemisorption mechanism (e.g., chemically treated activated carbon), in which the molecular contaminant and the reagent react to form a solid by-product at the surface of the activated carbon.

The chemisorption mechanisms available for use inside clean environments has been limited by the need to select chemical reagents that do not contribute contamination to the airstreams (i.e., the reagents and their by-products are solids under normal operating conditions). This has prevented the use of reagents that are highly effective at removing especially troublesome molecular contaminates that impose severe limitations on semiconductor device processes.

As used herein, the "normal operating conditions" of a clean environment are characterized by temperatures between 68° F. and 70° F. and a relative humidity of 40%.

SUMMARY

In one aspect, the invention features an air filtering system for filtering an air stream for use in a clean environment to effectively remove a process-limiting molecular contaminant therefrom comprising sequentially arranged upstream and downstream air filtering beds. The upstream air filtering bed is positioned to receive the air stream from the clean environment and comprises an upstream reagent selected to effectively remove the process-limiting molecular contaminant from the air stream as the air stream passes through the upstream air filtering bed, the upstream reagent releasing a characteristic volatile component into the air stream in sufficient quantity to be detrimental to the clean environment. The downstream air filtering bed is positioned to receive the air stream that has passed through the upstream air filtering bed and comprises a downstream reagent selected to remove the characteristic volatile component released by the upstream reagent into the air stream.

We have discovered that trace quantities, e.g., on the order of parts per trillion (ppt) of certain molecular contaminants can severely limit many clean environment processes. For example, deep ultraviolet (e.g., at operating wavelengths of 248 nm or 193 nm) photolithography systems can be process-limited by the presence of about 600 ppt of proton accepting contaminants such as ammonia and NMP. The present invention allows for the use of higher-performing chemical reagents (e.g., sulfuric acid) for removing such process-limiting contaminants that would otherwise be unusable due to their volatility or some other chemical, physical, or reactive property.

Among the embodiments of the invention are the following. The upstream reagent may be sulfuric acid and the downstream reagent may be a base (e.g., potassium hydroxide or potassium iodide). The air stream of the clean environment may be subject to molecular contamination including airborne proton acceptors and the upstream reagent may be selected to remove the airborne proton acceptors from the airstreams. The upstream reagent may off-gas at a level detrimental to processes conducted within the clean environment under normal operating conditions. The upstream reagent may be selected to remove amines from the airstream. The upstream reagent may be impregnated on activated carbon particles at a doping level of preferably 5–90%, and more preferably 20–50%. The downstream reagent may preferably be impregnated on activated carbon particles at a doping level of 5–15%. The upstream and downstream reagents may be preferably impregnated on activated carbon particles in the size range of 20×140 mesh and more preferably in the size range of 20×50 mesh. The upstream and downstream air filtering beds may respectively comprise a molecular chemical filter of the pleated filter type comprising an air permeable, relatively thick web of non-woven fibrous carrier material of pleated form, the web comprising a matrix formed of a large multiplicity of synthetic fibers and characterized in that activated carbon particles are distributed throughout the web, bound in the interstices of the matrix in a manner preventing loss to the air stream particles in quantity substantially detrimental to the clean environment. The upstream and downstream air filtering beds may be integrated into a common pleated non-woven carrier material. An intermediate air filtering bed may be disposed between the upstream and downstream air filtering beds and preferably comprises an intermediate reagent selected to remove the characteristic volatile component released by the upstream reagent or the process-limiting molecular contaminant from the air stream.

In another aspect, the invention features an air filtering system for filtering an air stream for use in a clean environment to effectively remove a process-limiting molecular contaminant including airborne proton acceptors therefrom comprising: an upstream air filtering bed positioned to receive the air stream from the clean environment comprising activated carbon particles in the size range of 20×140 mesh impregnated with sulfuric acid for effectively removing the airborne proton acceptors from the airstream as the air stream passes through the upstream air filtering bed; and a downstream air filtering bed positioned to receive the air stream that has passed through the upstream air filtering bed and comprising activated carbon particles in the size range of 20×140 mesh impregnated with a base.

According to another aspect, the invention features a clean environment that is substantially free of a detrimental molecular contaminant comprising: a processing station that releases a process-limiting molecular contaminant into the air stream; a recirculating air system for recirculating and filtering the airstream from adjacent the processing station, the recirculating air system comprising an air filtering system comprising an upstream air filtering bed positioned to receive the air stream recirculated by the recirculating air system and comprising an upstream reagent selected to effectively remove the process-limiting molecular contaminant released by the processing station from the air stream as the air stream passes through the upstream air filtering bed, the upstream reagent releasing a characteristic volatile component into the air stream in sufficient quantity to be detrimental to the clean environment, and a downstream air filtering bed positioned to receive the air stream that has passed through the upstream air filtering bed and comprising a downstream reagent selected to remove the characteristic volatile component released by the upstream reagent into the air stream.

Certain embodiments according to this aspect preferably further comprise a make-up air system for drawing air from an atmosphere that may be subject to a molecular contaminant including airborne proton acceptors. The makeup air system preferably comprises an air filtering system comprising an upstream air filtering bed positioned to receive the air stream recirculated by the recirculating air system and comprising an upstream reagent selected to effectively remove airborne proton acceptors from the air stream as the air stream passes through the upstream air filtering bed, the upstream reagent releasing a characteristic volatile component into the air stream in sufficient quantity to be detrimental to the clean environment, and a downstream air filtering bed positioned to receive the air stream that has passed through the upstream air filtering bed and comprising a downstream reagent selected to remove the characteristic volatile component released into the air stream by the upstream reagent of the upstream air filtering bed in the make-up air system.

In another aspect, the invention features a deep UV photolithography station comprising: a deep UV lithographic processing station; a recirculating air system for recirculating and filtering an airstream from adjacent the lithographic processing station, the recirculating air system comprising an air filtering system comprising an upstream air filtering bed positioned to receive the air stream recirculated by the recirculating air system and comprising activated carbon particles in the size range of 20×140 mesh impregnated with sulfuric acid for effectively removing airborne proton acceptors from the air stream as the air stream passes through the upstream air filtering bed, and a downstream air filtering bed positioned to receive the air stream that has passed through the upstream air filtering bed comprising activated carbon particles in the size range of 20×140 mesh impregnated with a base selected to remove volatile sulfuric acid or sulfuric acid components released into the air stream.

Other features and advantages will become apparent from the following description and the claims.

DESCRIPTION

Figure 1:
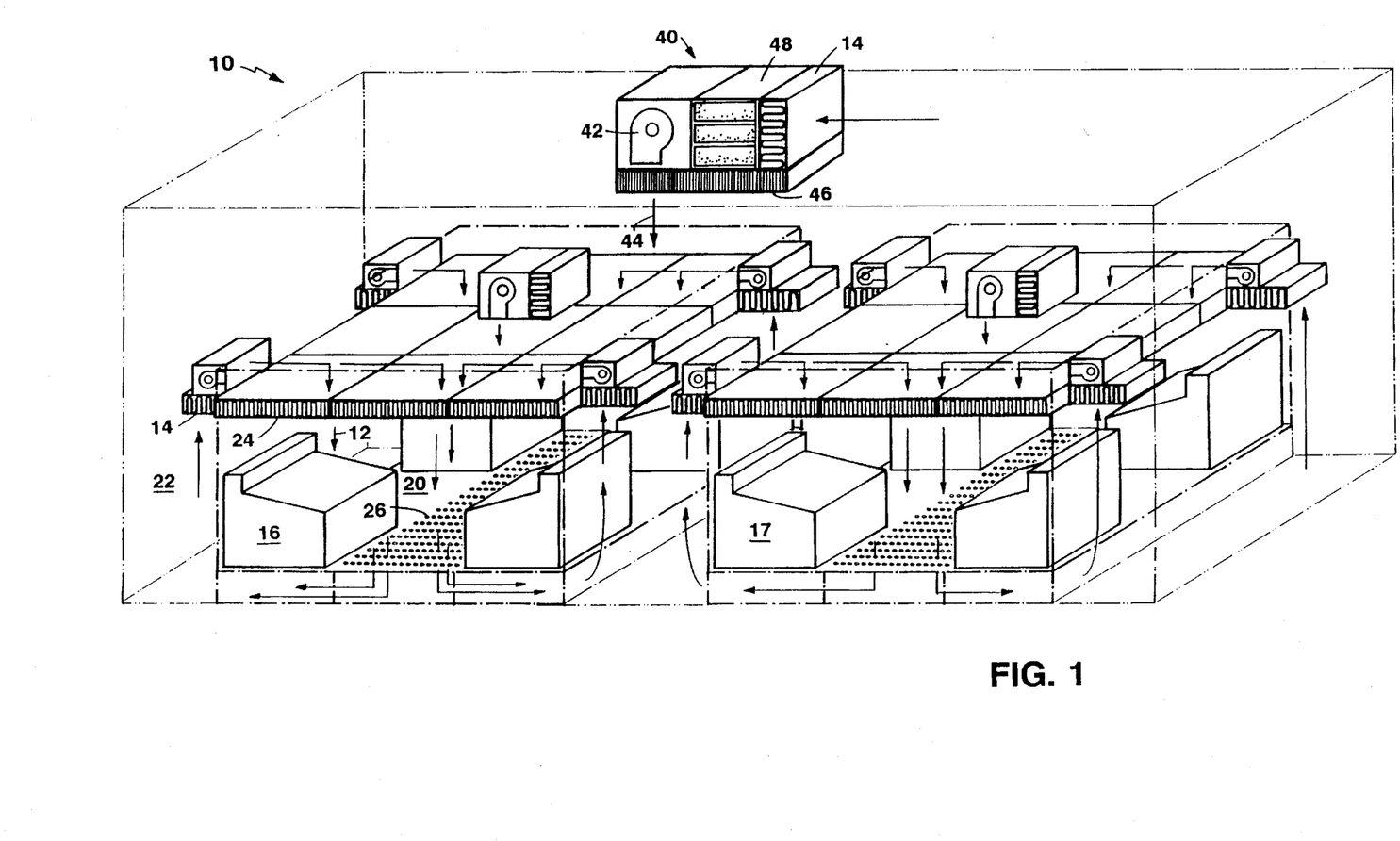
FIGS. 1 and 1A are a perspective view and a diagrammatic side view of a clean room.
Figure 1A:
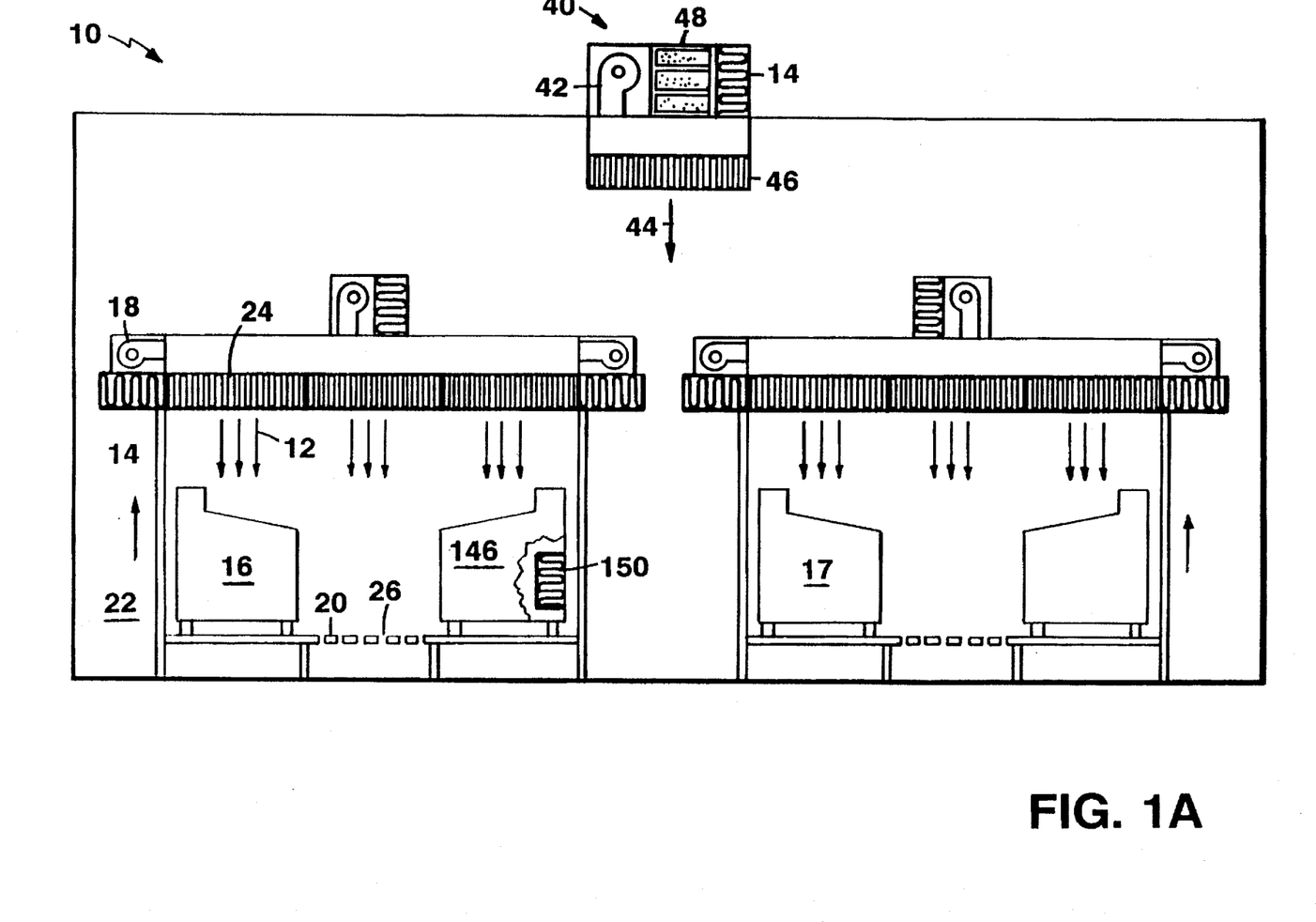

Referring to FIGS. 1 and 1A, inside a clean room 10 molecular contaminants (too small to be shown) in recirculating air streams 12 are removed by chemically active molecular air filtering systems 14, at least some of which having sequentially arranged upstream and downstream air filtering beds selected for effective targeted removal of process-limiting molecular contamination from the air streams in a manner reducing self-contamination and cross-contamination of process stations 16 (e.g., a conventional semiconductor photolithography station 17, although other processing stations are contemplated including etch, chemical vapor deposition, thin film deposition, developing, epitaxy and diffusion stations). Such process-limiting molecular contaminants may be released into the recirculating air streams by process stations 16.

Each processing station 16 is associated with a recirculating air handling system that generates recirculating air streams 12 (e.g., with air blowers 18). An air stream 12 follows a path which includes, a process station 16, a floor 20, a common air plenum 22, an air filtering system 14, and a high efficiency particulate air (HEPA) filter 24 used to remove particulate contamination (e.g., dust, lint, and other debris) from the air stream. The floor 20 is a conventional clean room floor that has air passages 26 to allow air streams 12 to pass therethrough.

The air stream recirculation rate is on the order of 10 interchanges per minute (on the order of 2000 cu.ft./minute)

to thoroughly filter the air streams even when the molecular filters are near the end of their respective service lives (i.e., when the filters have a low efficiency, defined by the formula (X-Y)/X wherein X is the upstream concentration of pollutant, and Y is the downstream concentration of pollutant). A higher recirculation rate can compensate for the inevitable decrease in efficiency. For example, after 10 air cycles a filter with a 30% efficiency may reduce the level of air contamination by 99%.

A make-up air handling system 40 is used to replace the air removed from the vicinity of the processing stations by the exhaust systems with air from, e.g., a sub-fab area. Air blower 42 generates the make-up air stream 44. A HEPA filter 46 is located downstream of the blower to prevent fine particulate contaminants from entering the common air plenum 22. An efficient (about 70%) particulate bag filter 48 is located upstream of the HEPA filter to reduce loading of the HEPA filter. A chemically active air filtering system 14, which generally has a particulate removal efficiency of about 30%, is located at an inlet port of the make-up air handling system to prevent premature loading of the bag and HEPA filters and filter molecular contamination from the incoming make-up air streams.

Filter Structure

Figure 2:
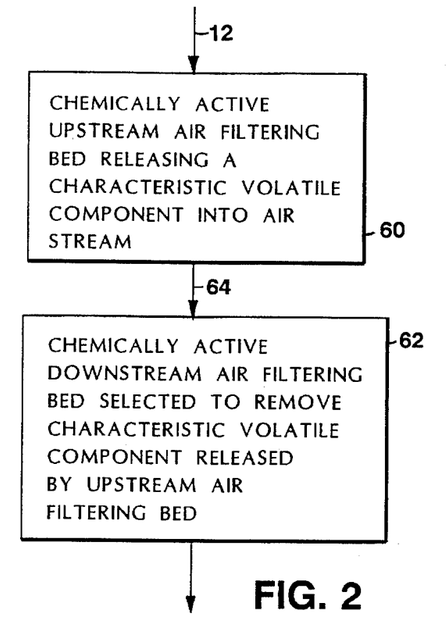
FIGS. 2–2D are schematic side views of molecular air filters having sequential air filtering beds.

Referring to FIG. 2, a chemically active air filtering system 14 is formed from separate sequentially arranged upstream and downstream air filtering beds 60, 62. The air filtering beds may be rack and tray-type filters or they may be fabric-based filters, described in detail below.

Upstream air filtering bed 60 is positioned to receive air streams 12 within the clean environment and includes an upstream reagent selected to effectively remove molecular contamination from the air streams as the air streams pass therethrough. The upstream reagent is selected based on its effectiveness for targeted removal of process-limiting molecular contamination and is not limited to those reagents that do not contribute contamination to the air streams. In fact, many effective reagents useful for targeted removal of molecular contamination tend to release volatile components (e.g., vapors resulting from volatilization of the reagent itself or volatile by-products resulting from the reaction between the reagent and a molecular contaminant) into air streams under normal operating conditions (e.g., temperatures between 68° F. and 70° F. and relative humidity of about 40%). The upstream air filtering bed typically includes adsorbent particles (e.g., activated carbon particles) that are impregnated with a reagent, which may release volatile components into the air streams in sufficient quantity to be detrimental to the clean room before, during or after airstreams containing molecular contamination pass through the upstream bed.

Downstream air filtering bed 62 is positioned to receive air streams 64 that have passed through the upstream air filtering bed and include a downstream reagent selected to remove the airborne components generated by the upstream reagent and released into the air streams. The doping level of the downstream reagent is selected to be sufficient to reduce the concentration level of the volatile component released by the upstream air filtering bed to a level that is not detrimental to an associated process within the clean environment. This level can be empirically determined.

This design allows for the use of higher performing reagents that would otherwise be unusable due to their volatility or some other chemical, physical, or reactive property that would contribute contamination to the clean room (e.g., the generation of unstable and volatile reaction by-products).

Figure 2A:
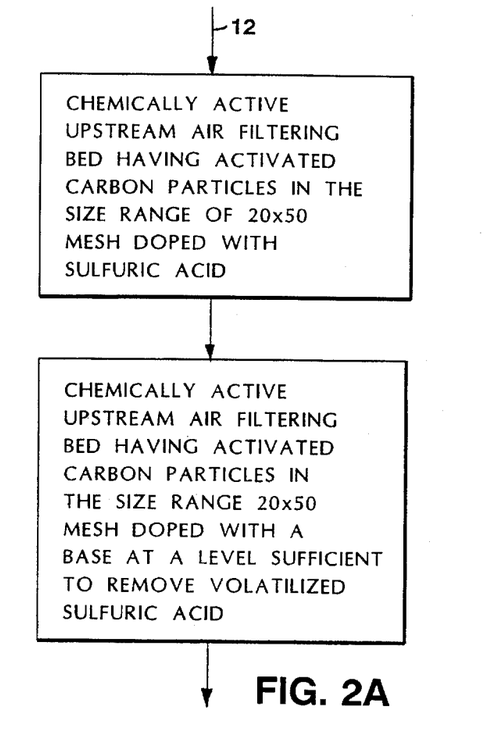

Referring to FIG. 2A, in a particularly important embodiment useful for filtering air streams associated with deep ultraviolet photolithography stations, the upstream chemically active air filtering bed includes activated carbon particles in the size range of 20×50 mesh doped with sulfuric acid. The downstream chemically active air filtering bed includes activated carbon particles in the size range of 20×50 mesh dopes with a base, such as KOH or KI, at a doping level sufficient to remove from air stream 12 volatilized sulfuric acid released by the upstream air filtering bed. Example 1, below, describes this embodiment in more detail.

Figure 2B:
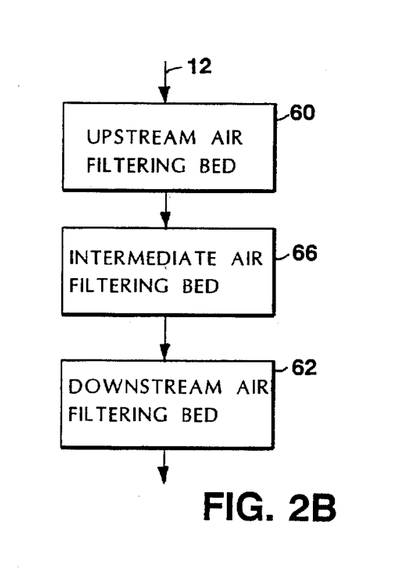

As shown in FIG. 2B, in alternative embodiment, air filtering systems 14 may include an intermediate filter 66 disposed between upstream and downstream filters 60, 62 to provide additional filtering of the air streams. Intermediate filter 66 may include a reagent selected to remove from the air streams an additional contaminant, not targeted by the upstream reagent, or to remove the volatile component released by the upstream air filtering bed. The reagent of the intermediate filter may itself release a volatile component into the air streams, in which case the downstream air filtering bed would include a reagent selected to remove this volatile component from the air stream. Other sequential arrangements of three or more molecular filters are possible, as long as air streams passing therethrough become substantially free of process-limiting molecular contamination.

Figure 2C:
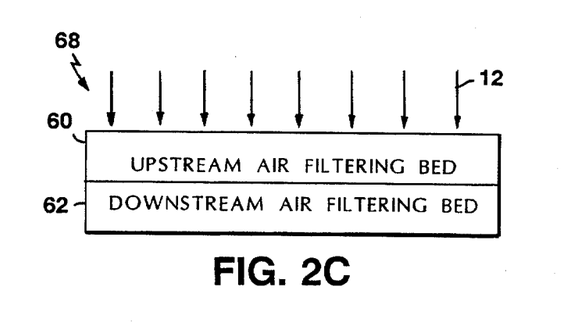
Figure 2D:
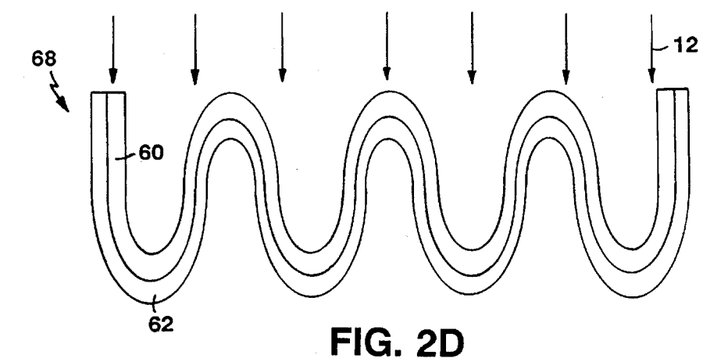

If fabric-based filters are used, upstream and downstream air filtering beds can be integrated into a single filter 68, as shown in FIG. 2C. This filter construction may be pleated as shown in FIG. 2D to increase the residence time of the air streams within the filter, increasing the efficiency of the filter.

Figure 3:
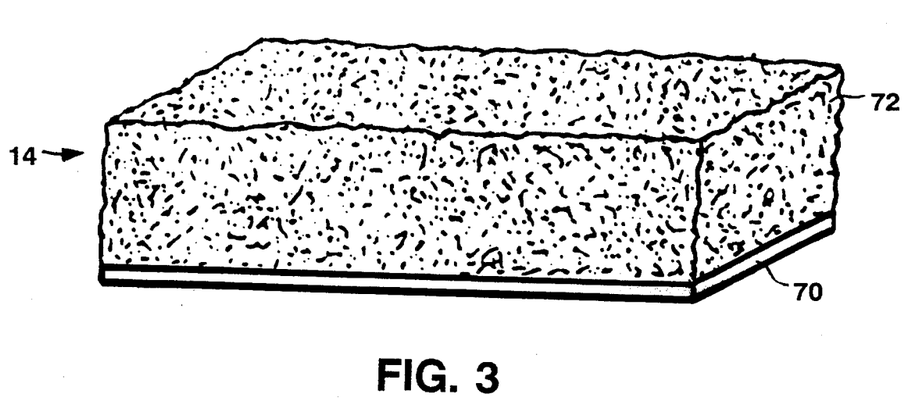
FIG. 3 is a diagrammatic side view in partial cross-section of an air filter including adsorbent particles contained within a web of non-woven fibers.

Referring to FIG. 3, in a preferred fabric-based filtering system embodiment, each air filtering bed is formed from a dense, needled, non-woven polyester batting 70 (or some other thermo-plastic material) of about 15 denier having a thickness of about ¼ inch. The batting is spray-bonded to a loose non-woven polyester batting 72 of approximately 6 denier having a thickness of approximately 1 inch. After bonding, the resulting carrier material has two distinct layers and a thickness of approximately 0.8 inch. Alternatively, the non-woven carrier may be formed from a polyester batting which is needled on one side thereby forming a single polyester batting having a dense layer on one side and a total thickness of about 0.8 inch. Adsorbent particles are applied to the carrier material from a vibrating support that evenly distributes the particles throughout the polyester batting. The adsorbent particles may be activated carbon particles that are chemically impregnated and retain their reactive and adsorptive capacity as a result of the dry processing used to create the filter. Alternatively, the adsorbent particles may be ion exchange resins. The resulting particle-loaded carrier material is heated and calendered under controlled conditions, as described in co-pending U.S. patent application Ser. No. 08/161,931, filed Dec. 2, 1993, which is herein incorporated by reference.

Figure 3A:
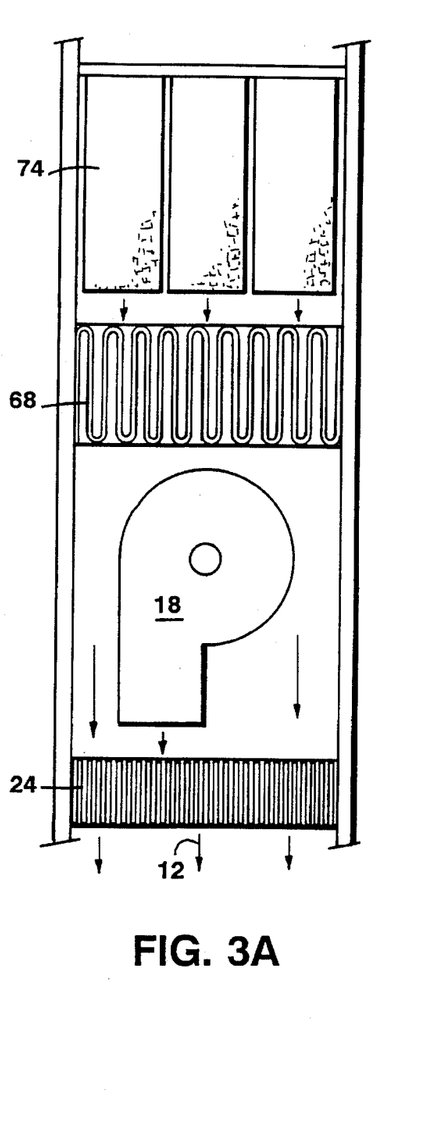
FIG. 3A is a diagrammatic side view of an air system including a pleated, fabric-based chemical air filter.

Referring to FIG. 3A, a pleated fabric-based air filter 68 (FIG. 2C) is located directly upstream of a HEPA filter 24 (i.e., there is no intervening filter between the HEPA filter and the chemical filter that would cause additional pressure drop to the air stream) inside the recirculating air systems of the clean room. A particulate bag filter 74 is positioned directly upstream of chemical filters 68 to remove particulates from the air streams that would tend to cover the adsorbent surfaces of the adsorbent particles, reducing their filtering effectiveness.

Figure 4:
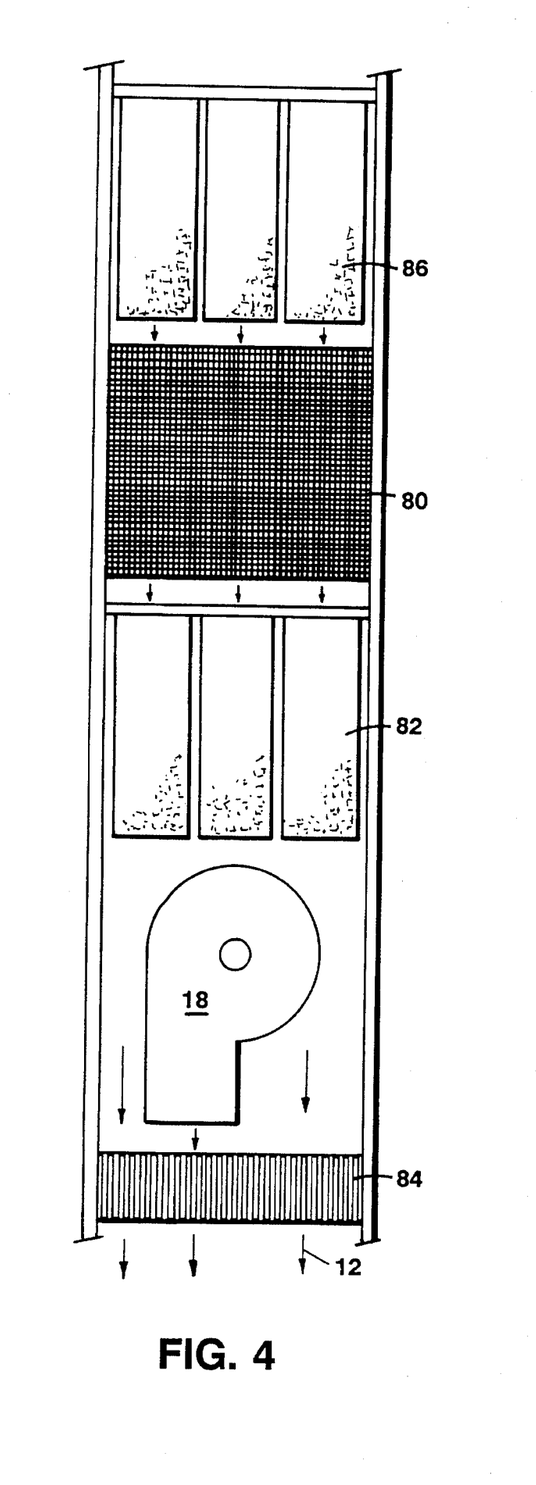
FIG. 4 is a diagrammatic side view of an air system including a rack and tray chemical air filter.

As mentioned above, an air filtering bed may instead be in the form of a conventional rack and tray filter 80, as shown in FIG. 4. Rack and tray filter 80 is formed from a perforated metal container, which is filled with adsorbent material (e.g., chemically treated activated carbon, chemically treated silica gel, chemically treated activated alumina, or any other chemically treated high surface high surface area carrier or platform) and has typical dimensions of 24 inches by 24 inches in face area by 29 inches in depth. A particle filter 82 (e.g., a bag filter) is located downstream of rack and tray filter 80 to capture the released particulate matter and to prevent rapid loading of HEPA filter 84, which is expensive and difficult to replace. An additional particulate filter 86 is employed directly upstream of the rack and tray filter 80 to further remove particulates from the air streams.

Adsorbent-based filters operate on the principles of diffusion and the diffusion gradient. Diffusion delivers the molecular contaminant to the surface of the adsorbent particles and provides the mechanism by which the contaminant penetrates the exterior surface of the particle. Diffusion in the airstream is a passive process whereby an area of high contaminant concentration moves to an area of relatively lower concentration on the adsorbent surface. The diffusion gradient is the concentration difference between a region of higher concentration (in the airstream or on the adsorbent surface) and a region of lower concentration (on the adsorbent surface or in the particle). The larger the diffusion gradient, the faster the movement process occurs. At low concentrations (less than 10 ppm), the diffusion gradient is low and diffusion into the adsorbent particle occurs at a rate much lower than the rate at which the filter loses efficiency (i.e., its ability to adsorb contaminants).

Therefore, when designing molecular air filtration systems for low concentration environments, it is important to maximize the external surface area of the adsorbent particles. This is accomplished by using very small adsorbent particles that have a very high surface area to mass ratio. This is especially important in chemisorptive systems in which molecular contaminants react to form solids at the surface of the adsorbent particles. Solids are less mobile and do not migrate appreciably into the particle center even under high contaminant concentrations. Maximizing the available surface area of the adsorbent particles by using small adsorbent particles allows for higher performing systems at a lower cost. Preferred sizes for activated carbon particles are in the range of 20×140 mesh, and more preferably in the range of 20×50 mesh.

In the design of the recirculating and make-up air handling systems it is desirable to achieve the lowest practical level of particulate and molecular contamination possible. However, a compromise must be reached between level of contamination and the cost of the clean room.

To achieve the lowest practical level of air contamination additional air filters could be added in series to all of the air handling systems. However, this would add to the total cost of the clean room in at least two ways. First, additional filters would cause an increase in pressure drop (i.e., resulting in reduction in the volume of air per unit time flowing in air stream 12 through filtering system 14) in the air handling systems and larger air blowers would be required to make up the loss in pressure. Second, the increase in the size of the blowers and the additional space taken up by the additional filters would require a larger and therefore more expensive clean room.

Targeted Removal

We have discovered that trace quantities, e.g., on the order of parts per trillion (ppt) of certain molecular contaminants can severely limit many clean environment processes. For example, deep ultraviolet (e.g., at operating wavelengths of 248 nm or 193 nm) photolithography systems can be process-limited by the presence of about 600 ppt of proton accepting contaminants, such as ammonia and NMP.

Figure 5:
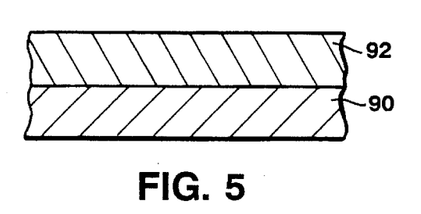
FIGS. 5–5B are diagrammatic side views of a semiconductor wafer bearing a layer of photoresist at different stages of photolithographic patterning.
Figure 5A:
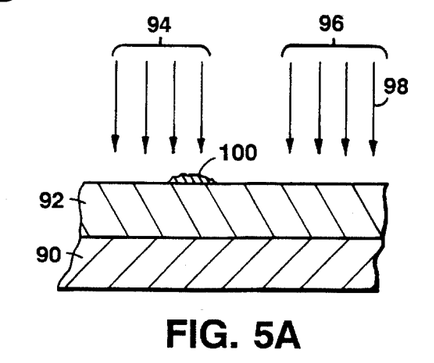
Figure 5B:
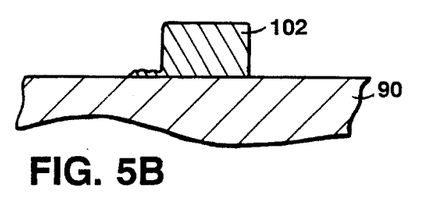

Referring to FIGS. 5–5B, in deep UV photolithography a substrate 90 (e.g., a semiconductor wafer) bearing a layer of photoresist 92 is patterned by selectively illuminating regions 94, 96 of photoresist layer 92 with deep UV radiation 98, which permits devices to be fabricated with submicron features (e.g., about 0.25–0.5 μm).

As shown in FIGS. 5A and 5B, if molecular contamination 100, which includes, e.g., a proton acceptor (e.g., a base such as ammonia and other reactive amines), is deposited on the surface of photoresist layer 92, the resulting photoresist pattern 102 (FIG. 5B) will be degraded from the desired pattern in a manner catastrophic for subsequent processing steps, thereby severely reducing the fabrication yield of the process. When UV light illuminates photoresist, an acid group is formed which begins the polymerization of the photoresist. When a proton acceptor deposits on the surface of the photoresist it reacts with the acid group, causing the polymerization process to terminate, preventing controlled polymerization of the photoresist.

We have realized that it is highly desirable to effectively remove process-limiting molecular contamination from airstreams within clean environments. The present invention allows for the use of higher performing chemical media treatments (reagents) that would otherwise be unusable due to their volatility or some other chemical, physical or reactive property.

Figure 6:
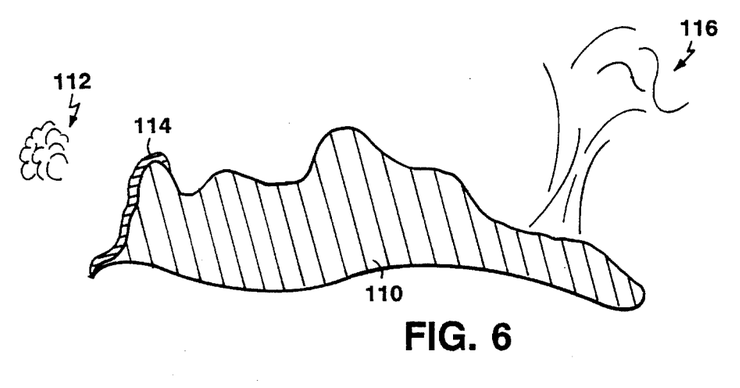
FIG. 6 is a diagrammatic side view of an adsorbent particle that has been impregnated with a reagent.

Referring to FIG. 6, an activated carbon particle 110 impregnated with a reagent (e.g., sulfuric acid) is exposed to airstreams containing molecular contamination 112, which reacts with the reagent to produce a solid by-product 114. The effectiveness of the molecular filter directly depends on the reactivity of the reagent selected to remove the targeted molecular contaminant. Unfortunately, some of the most highly reactive reagents exhibit some vapor pressure, under normal operating conditions, and therefore tend to generate and release into air streams molecular components 116 that would be detrimental to many clean room processes. Furthermore, some reactive reagents react with molecular contamination to produce unstable by-products that may sublime at normal operating temperatures (68°–70° F.).

Example 1

For the effective targeted removal of ammonia and other reactive amines from the vicinity of a deep UV photolithography station, molecular air filters having upstream and downstream air filtering beds are installed in the recirculation and make-up air systems associated with the photolithography station. The upstream air filtering bed includes activated carbon particles in the size range of 20×140 mesh, and preferably 20×50 mesh, impregnated with sulfuric acid at a doping level of 5–90%, and more preferably between 20% and 50%. The sulfuric acid reacts with amine contamination ($R(NH_4)$) to produce a solid by-product at the surface of the activated carbon particles:

The downstream air filtering bed includes activated carbon particles in the size range of 20×140 mesh, more preferably between 20×50 mesh, impregnated with a downstream reagent selected to remove acid-based contamination, e.g., a base, such as potassium hydroxide at a doping level of 5–15%, or a chemical from the following group: KI, $K_2CO_3$, NaOH, and $Na_2CO_3$.

Example 2

For the effective removal of proton donors or acid gases, such as $SO_2$, $NO_2$, HCl, and $Cl_2$, and dopants such as arsine and phosphine from the vicinity of a deep UV photolithography station, molecular air filters having upstream and downstream air filtering beds are installed in the recirculation and make-up air systems associated with the photolithography station. The upstream air filtering bed includes whetlerite carbon. Whetlerite is chemically treated media using a combination of ammonia and transition metal oxides. The active chemicals on the whetlerite surface act as an oxidant or complexing agent and reacts with the proton donors or acid gases to form a solid by-product. Under normal operating conditions, ammonia may be released from the carbon surface. The downstream air filtering bed includes activated carbon particles in the size range of 20×140 mesh, preferably between 20×50 mesh, impregnated with a metal salt or acid, e.g., zinc chloride, copper sulfate, sulfuric acid, phosphoric acid, hydrochloric acid, and copper chloride.

Other embodiments are within the scope of the claims.

For example, an activated carbon chemically active molecular air filtering system 150 (FIG. 1A) having sequentially arranged upstream and downstream air filtering beds may be installed inside a processing station 146 which has an independent air handling system.

It is also contemplated that each processing station 16 may be self-contained (a so-called "mini-environment") and include its own respective air handling system, instead of sharing a common clean environment (e.g., a clean room) with other processing stations.

What is claimed is:

1. An air filtering system for filtering an air stream for use in a clean environment to effectively remove a process-limiting molecular contaminant therefrom comprising sequentially arranged upstream and downstream air filtering beds, said upstream air filtering bed being constructed and arranged for filtering air for use in a clean environment, being positioned to receive an air stream from the clean environment and comprising activated carbon particles in the size range of 20×140 mesh impregnated with an upstream chemically active reagent of sulfuric acid in a quantity selected to reduce the concentration of a process-limiting molecular contaminant in the air stream to a level below that which is detrimental to a process associated with the clean environment as said air stream passes through the upstream air filtering bed, said upstream chemically active reagent releasing a characteristic volatile component into said air stream at a concentration level that is detrimental to the associated clean environment process, and said downstream air filtering bed being constructed and arranged to filter air for use in a clean environment, being positioned to receive the air stream that has passed through said upstream air filtering bed and comprising activated carbon particles in the size range of 20×140 mesh impregnated with a downstream reagent selected to reduce the concentration of the characteristic volatile component released by said upstream reagent of sulfuric acid to a level below that which is detrimental to the associated clean environment process.

2. The air filtering system of claim 1 wherein said downstream reagent is a base.

3. The air filtering system of claim 1 wherein said sulfuric acid is impregnated on activated carbon particles at a doping level of 5–90%.

4. The air filtering system of claim 3 wherein said doping level is 20–50%.

5. The air filtering system of claim 1 wherein said downstream reagent is potassium hydroxide or potassium iodide.

6. The air filtering system of claim 5 wherein said downstream reagent is impregnated on activated carbon particles at a doping level of 5–15%.

7. The air filtering system of claim 1 wherein the air stream of the clean environment is subject to molecular contamination including airborne proton acceptors and said upstream reagent comprises sulfuric acid impregnated on an adsorbent media at a doping level selected to remove the airborne proton acceptors from the airstream as the air stream passes through said upstream air filtering bed.

8. The air filtering system of claim 1 wherein said upstream and downstream reagents are impregnated on activated carbon particles in the size range of 20×50 mesh.

9. The air filtering system of claim 1 wherein said upstream and downstream air filtering beds respectively comprise a molecular chemical filter comprising an air permeable web of non-woven fibrous carrier material of pleated form, said web comprising a matrix formed of a multiplicity of synthetic fibers and characterized in that activated carbon particles are distributed throughout said web, bound in the interstices of the matrix in a manner preventing loss to the air stream particles in quantity detrimental to the clean environment.

10. The air filtering system of claim 1 wherein said upstream and downstream air filtering beds are integrated into a common pleated non-woven carrier material.

11. The air filtering system of claim 1 further comprising an intermediate air filtering bed disposed between said upstream and downstream air filtering beds and comprising an intermediate reagent selected to remove the volatile component released by said upstream reagent.

12. The air filtering system of claim 1 further comprising an intermediate air filtering bed disposed between said upstream and downstream air filtering beds and comprising an intermediate reagent selected to remove the process-limiting molecular contaminant from said air stream.

13. The filtering system of claim 1 wherein said upstream reagent releases into the air stream said characteristic volatile component at a concentration of about 600 ppt or greater.

14. An air filtering system for filtering an air stream for use in a clean environment to effectively remove a process-limiting molecular contaminant therefrom comprising sequentially arranged upstream and downstream air filtering beds, said upstream air filtering bed being constructed and arranged for filtering air for use in a clean environment, being positioned to receive an air stream from the clean environment and comprising whetlerite to reduce the concentration of a process-limiting molecular contaminant in the air stream to a level below that which is detrimental to a process associated with the clean environment as said air stream passes through the upstream air filtering bed, said whetlerite releasing a characteristic volatile component into said air stream at a concentration level that is detrimental to the associated clean environment process, and said downstream air filtering bed being constructed and arranged to filter air for use in a clean environment, being positioned to receive the air stream that has passed through said upstream air filtering bed and comprising activated carbon particles in the size range of 20×140 mesh impregnated with downstream reagent selected to reduce the concentration of the characteristic volatile component released by said whetlerite to a level below that which is detrimental to the associated clean environment process.

15. The air filtering system of claim 14 wherein the downstream reagent is a metal salt.

16. The air filtering system of claim 14 wherein the downstream reagent is an acid suitable for exposure to air for use in a clean environment.

17. The filtering system of claim 14 wherein said upstream reagent releases into the air stream said characteristic volatile component at a concentration of about 600 ppt or greater.

18. An air handling system for providing a filtered air stream, substantially free of a process-limiting molecular contaminant, for use in a clean environment comprising:

a semiconductor device processing station that releases a process-limiting molecular contaminant into air within a clean environment;

a recirculating air system for recirculating and filtering an airstream from adjacent said processing station, said recirculating air system comprising an air filtering system comprising sequentially arranged upstream and downstream air filtering beds, said upstream air filtering bed being constructed and arranged to filter air for use in a clean environment, being positioned to receive the air stream recirculated by said recirculating air system and comprising activated carbon particles in the size range of 20×140 mesh impregnated with an upstream reagent of sulfuric acid in a quantity selected to reduce the concentration of the process-limiting molecular contaminant released by said semiconductor device processing station from the air stream as the air stream passes through said upstream air filter, said upstream reagent releasing a characteristic volatile component into the air stream at a concentration level that is detrimental to the clean environment, and said downstream air filtering bed being constructed and arranged to filter air for use in a clean environment, being positioned to receive the air stream that has passed through said upstream air filtering bed and comprising activated carbon particles in the size range of 20×140 mesh impregnated with a downstream reagent selected to reduce the concentration of the characteristic volatile component released by said upstream reagent of sulfuric acid to level below that which is detrimental to the associated clean environment process.

19. The clean environment of claim 18 further comprising a make-up air system for drawing air from an atmosphere that is subject to molecular contamination including airborne proton acceptors, said make-up air system comprising an air filtering system comprising an upstream air filtering bed positioned to receive air streams recirculated by said recirculating air system and comprising an upstream reagent selected to effectively remove airborne proton acceptors from the air stream as the air stream passes through said upstream air filter, said upstream reagent releasing a characteristic volatile component into the air stream, and a downstream air filtering bed positioned to receive the air stream that has passed through said upstream air filtering bed and comprising a downstream reagent selected to remove the characteristic volatile component released into said air stream by said upstream reagent of the upstream air filtering bed in said make-up air system.

20. The filtering system of claim 18 wherein said upstream reagent releases into the air stream said characteristic volatile component at a concentration of about 600 ppt or greater.

21. A deep UV photolithography station comprising a deep UV lithographic process tool;

a recirculating air system for recirculating and filtering an airstream from adjacent said lithographic processing station, said recirculating air system comprising an air filtering system comprising an upstream air filtering bed positioned to receive the air stream recirculated by said recirculating air system and comprising activated carbon particles in the size range of 20×140 mesh impregnated with sulfuric acid for effectively removing airborne proton acceptors from the air stream as the air stream passes through said upstream air filtering bed, and a downstream air filtering bed positioned to receive the air stream that has passed through said upstream air filtering bed and comprising activated carbon particles in the size range of 20×140 mesh impregnated with a base selected to remove volatile sulfuric acid or sulfuric acid components released into said air stream.

22. The deep UV photolithography station of claim 21 further comprising a make-up air system for drawing air from an atmosphere that may be subject to a molecular contaminant including airborne proton acceptors, said makeup air system comprising an air filtering system comprising an upstream air filtering bed positioned to receive the air stream recirculated by said recirculating air system and comprising an upstream reagent selected to effectively remove airborne proton acceptors from the air stream as the air stream passes through said upstream air filtering bed, said upstream reagent releasing a characteristic volatile component into the air stream in sufficient quantity to be detrimental to the clean environment, and a downstream air filtering bed positioned to receive the air stream that has passed through said upstream air filtering bed and comprising a downstream reagent selected to remove the characteristic volatile component released by said upstream reagent into said air stream.

23. The air filter of claim 21 wherein said upstream reagent is impregnated on activated carbon particles at a doping level of between 5% and 90%.

24. The air filter of claim 23 wherein said doping level is between 20% and 50%.

25. An air filtering system comprising at least two chemically active air filtering beds in sequence along an air stream associated with a clean environment, said system comprising a first chemically active air filtering bed, constructed and arranged to filter air for use inside a clean environment, comprising activated carbon particles in the size range of 20×140 mesh impregnated with a reagent of sulfuric acid in a quantity selected to reduce the concentration of a first contaminant in an air stream associated with a clean environment to a level that is below that which is detrimental to a process associated with the clean environment, said reagent of sulfuric acid having the characteristic of releasing a contaminant into the air stream that is different from said first contaminant, a downstream chemically active air filtering system, constructed and arranged to filter air for use in a clean environment, comprising activated carbon particles in the size range of 20×140 mesh impregnated with a reagent having the characteristic of reducing the concentration of the contaminant released by said sulfuric acid reagent to a level that is below that which is detrimental to the associated clean environment, wherein the chemically active air filtering beds in said system are selected and cooperatively arranged so that said air filtering system has removed from the air stream said first contaminant and any volatile contaminants detrimental to said clean environment released by said system.

26. The filtering system of claim 25 wherein said upstream reagent of sulfuric acid releases into the air stream said characteristic volatile component at a concentration of about 600 ppt or greater.

27. A method for filtering an air stream for use in a clean environment to reduce the concentration of a process-limiting molecular contaminant therein to a level below that which is detrimental to a process associated with the clean environment, said method comprising the steps of:

providing an upstream air filtering bed within an air handling system of a clean environment to receive an air stream from the clean environment, said upstream air filtering bed comprising an upstream chemically active reagent in a quantity selected to reduce the concentration of a process-limiting molecular contaminant in the air stream to a level below that which is detrimental to a process associated with the clean environment as said air stream passes through the upstream air filtering bed, said upstream chemically active reagent releasing a characteristic volatile component into said air stream at a concentration level that is detrimental to the associated clean environment process, and providing a downstream air filtering bed within the air handling system of the clean environment to receive the air stream that has passed through said upstream air filtering bed, said downstream air filtering bed comprising a downstream reagent selected to reduce the concentration of the characteristic volatile component released by said upstream reagent to a level below that which is detrimental to the associated clean environment process.

28. The method of claim 27 wherein the upstream air filtering bed that is provided comprises activated carbon particles in the size range of 20×140 mesh impregnated with sulfuric acid.

29. The method of claim 28 wherein the downstream air filtering bed that is provided comprises activated carbon particles in the size range of 20×140 mesh impregnated with a base.

30. The method of claim 29 wherein the activated carbon particles of the downstream air filtering bed are impregnated with potassium hydroxide.

31. The method of claim 29 wherein the activated carbon particles of the downstream air filtering bed are impregnated with potassium iodide.

32. The method of claim 27 wherein said upstream air filtering bed that is provided releases into the air stream said characteristic volatile component at a concentration level of about 600 ppt or greater.

33. The method of claim 27 wherein said upstream reagent that is provided has a higher vapor pressure than water under normal operating conditions.

34. The method of claim 27 wherein said upstream reagent that is provided off-gases at a level that is detrimental to processes conducted within the clean environment under normal operating conditions.

35. The method of claim 27 wherein the upstream reagent that is provided is selected to reduce the concentration of amines from the air stream as the air stream passes through said upstream air filtering bed.

* * * * *